United States Patent
Eubisch et al.

(10) Patent No.: US 11,339,416 B2
(45) Date of Patent: May 24, 2022

(54) INLINE SENSOR ARRANGEMENT, AND METHOD FOR PRODUCING AND COMMISSIONING SAID INLINE SENSOR ARRANGEMENT

(71) Applicant: Endress+Hauser Conducta GmbH+Co. KG, Gerlingen (DE)

(72) Inventors: Angela Eubisch, Chemnitz (DE); Michael Hanko, Dresden (DE)

(73) Assignee: ENDRESS+HAUSER CONDUCTA GMBH+CO. KG, Gerlingen (DE)

( * ) Notice: Subject to any disclaimer, the term of this patent is extended or adjusted under 35 U.S.C. 154(b) by 942 days.

(21) Appl. No.: 15/986,344

(22) Filed: May 22, 2018

(65) Prior Publication Data
US 2018/0334698 A1  Nov. 22, 2018

(30) Foreign Application Priority Data
May 22, 2017  (DE) ................... 10 2017 111 141.7

(51) Int. Cl.
| | | |
|---|---|---|
| *C12Q 1/00* | (2006.01) | |
| *A61L 2/28* | (2006.01) | |
| *G01N 27/28* | (2006.01) | |
| *A61L 2/07* | (2006.01) | |

(52) U.S. Cl.
CPC .............. *C12Q 1/006* (2013.01); *A61L 2/07* (2013.01); *A61L 2/28* (2013.01); *G01N 27/283* (2013.01); *A61L 2202/14* (2013.01)

(58) Field of Classification Search
None
See application file for complete search history.

(56) References Cited

U.S. PATENT DOCUMENTS 4,343,688 A * 8/1982 Harwood ............. G01N 27/121
204/430
6,516,677 B1   2/2003 Suter
(Continued)

FOREIGN PATENT DOCUMENTS

| CN | 2190995 Y | 3/1995 |
|---|---|---|
| CN | 2769851 Y | 4/2006 |

(Continued)

*Primary Examiner* — Brian R Gordon
(74) *Attorney, Agent, or Firm* — Mark A. Logan; Endress+Hauser (USA) Holding, Inc.

(57) ABSTRACT

The present disclosure relates to an inline sensor arrangement for the detection of measurement values of a measurand representing an analyte content of a measuring medium, which arrangement comprises: a sensor which is designed to generate and output a measurement signal correlated with the measurand, wherein the sensor has at least one sterile sensor element provided for contact with the measurement medium; and a housing surrounding the at least one sensor element, which housing encloses the sensor element in a chamber sealed tightly against an environment of the housing, and wherein the chamber contains inside it a gas volume that is designed such that an influence of harmful substances—in particular, of reactive nitrogen and/or oxygen species—on the at least one sensor element is largely prevented. The present disclosure further relates to a method for the production of said inline sensor arrangement, and for its commissioning.

21 Claims, 5 Drawing Sheets

(56) References Cited

U.S. PATENT DOCUMENTS

| | | | | |
|---|---|---|---|---|
| 6,561,012 | B1* | 5/2003 | Sadler | G01N 25/56 |
| | | | | 73/76 |
| 10,962,469 | B2* | 3/2021 | Rudmann | G01N 25/56 |
| 2004/0108472 | A1* | 6/2004 | Maruo | G01N 21/552 |
| | | | | 250/504 R |
| 2005/0141587 | A1* | 6/2005 | Muhlig | G01K 17/006 |
| | | | | 374/31 |
| 2010/0166603 | A1 | 7/2010 | Opie | |
| 2010/0293892 | A1* | 11/2010 | Curry | B65D 81/2084 |
| | | | | 53/403 |
| 2012/0091326 | A1 | 4/2012 | Baumfalk et al. | |
| 2012/0152765 | A1 | 6/2012 | Trapp et al. | |
| 2021/0025849 | A1* | 1/2021 | Zhang | G01N 27/626 |

FOREIGN PATENT DOCUMENTS

| | | |
|---|---|---|
| CN | 102564619 A | 7/2012 |
| CN | 103811932 A | 5/2014 |
| CN | 203642882 U | 6/2014 |
| CN | 106489049 A | 3/2017 |
| DE | 102008054551 A1 | 6/2009 |
| DE | 102009037345 A1 | 12/2010 |
| DE | 102010001876 A1 | 8/2011 |
| DE | 102009050448 A1 | 12/2011 |
| DE | 102014101759 A1 | 8/2015 |
| DE | 102016000997 B3 | 2/2017 |
| DE | 102015116355 A1 | 3/2017 |

* cited by examiner

INLINE SENSOR ARRANGEMENT, AND METHOD FOR PRODUCING AND COMMISSIONING SAID INLINE SENSOR ARRANGEMENT

CROSS-REFERENCE TO RELATED APPLICATION

The present application is related to and claims the priority benefit of German Patent Application No. 10 2017 111 141.7, filed on May 22, 2017, the entire contents of which are incorporated herein by reference.

TECHNICAL FIELD

The present disclosure relates to an inline sensor arrangement for the detection of measurement values of a measurand representing an analyte content of a measuring medium. The present disclosure further relates to a method for the production of said inline sensor arrangement, and for its commissioning.

BACKGROUND

In order to determine the composition of measuring media—in particular, liquids, e.g., pure liquids, liquid mixtures, emulsions, or suspensions—various analytical measuring devices are used in process metrology and analysis metrology. An analytical measuring device generally comprises a sensor which is designed to generate an electrical measurement signal dependent upon at least one analytical measurand, as well as an electronic evaluation device which, from the measurement signal, determines a measurement value representing the current value of the at least one analytical measurand in the measuring medium. The analytical measurand can, for example, be a concentration or activity of an analyte or a parameter dependent upon a concentration or activity of at least one analyte in the measuring medium. An analyte here means one or more substances contained in and, in particular, dissolved in the measuring medium, whose concentration in the measuring medium is to be determined or monitored by the sensor. The electronic evaluation device can be at least partially integrated into a measuring transducer arranged directly at the measurement point, which transducer has a housing with display and input elements. At least one part of the electronic evaluation device may also be arranged together with the sensor in a common housing.

Such analytical measuring devices are used in a variety of fields, e.g., for monitoring and controlling processes in pharmaceutical, chemical, biotechnical, or biochemical production, but also in processes for water conditioning or sewage purification, and in environmental analysis. Insofar as an analytical measuring device is used in a process, the measuring medium will typically be contained in a process vessel. Such a process vessel may, for example, be a pipeline of a process plant or a reaction vessel—for example, a fermentor.

Sensors that are integrated into the wall of a process vessel for monitoring a measurand of a measuring medium contained in the process vessel are referred to as inline sensors. An inline sensor detects the measurand directly in the measuring medium to be monitored. With inline sensors, an extraction and pre-treatment of a sample from the process is therefore not necessary for determining an analytical measurand. For the integration of a sensor into the process wall, diverse adapters and fittings—in particular, immersion or retractable fittings—are known. An arrangement that comprises an inline sensor integrated into the wall of a process vessel and, if applicable, an electronic evaluation device connected to the inline sensor, but, offset from this, is referred to as an inline sensor arrangement. The inline sensor may be fixed in the wall by means of a suitable adapter.

With processes that must be implemented under sterile or aseptic conditions—for example, as they occur in biotechnology, pharmaceutics, or food technology—all parts of the process plant that come into contact with the process media—in particular, all process vessels and also the sensors integrated therein—are typically sterilized (for example, thermally, via heat) before the beginning of the process or between individual process steps. The heat sterilization may take place via dry heat (typically, with hot air between 160° C. and 180° C. as a sterilization medium) or via superheated steam as sterilization medium under increased pressure, e.g., via autoclaving in a pressure vessel—what is known as an autoclave. For example, superheated steam sterilization methods are common in which temperatures of at least 120° C. or more may occur. If the heat sterilization is performed in an autoclave, the process-contacting parts of the process plant—possibly already connected to one another—are introduced into the autoclave and are sterilized there. The sterilized parts are subsequently removed from the autoclave again and placed in operation. Alternatively, a process plant may be sterilized by means of what is known as an SIP method (SIP is the acronym for the English technical term, "sterilization in place"), in which the process vessel to be sterilized, including the inline sensor arrangements integrated therein, is sterilized with superheated steam that is introduced into the process vessel over a predetermined time period. Therefore, inline sensor arrangements must be able to withstand the conditions that thereby occur, such as high temperatures and increased pressures, without loss of functionality.

In bioprocess metrology, e.g., for monitoring, controlling, and/or regulating biotechnology processes, sensors are also used that have biological detection elements, e.g., those that—possibly as receptors—selectively and specifically bind to the analyte. Biological detection elements may be proteins such as enzymes or antibodies, DNA/RNA fragments, cell organelles, or whole cells and microorganisms. Such sensors are designated as biosensors. After a typical, superheated steam sterilization process, the receptors or biological detection elements of such biosensors are normally present with starkly reduced activity—most often, irreversibly denatured, i.e., their native 3-D structure (conformation) is destroyed. Such biosensors therefore, in principle, may not be used as inline sensors in the wall of a process vessel and be sterilized with this by means of a typical SIP method, without taking further measures.

Many sensors with biological detection elements, e.g., those that originate from mesophilic organisms which live in a temperature range of approximately 20-45° C., may not be exposed to increased temperatures under SIP conditions, e.g., of 80° C., in order to not lose their functionality.

Sterilizable biosensors based upon amperometric enzyme sensors are described in the literature. In M. Phelps, *Development of a regenerable glucose biosensor probe for bioprocess monitoring*, master's thesis, University of British Columbia, 1993, an overview of the literature regarding such sensors is given. Strategies described therein for ensuring sterilization capability of such biosensors while maintaining their functionality include the introduction of the temperature-sensitive receptors arranged on a carrier—said carrier comprising, for example, a working electrode—only after the sterilization process in a reaction chamber within a sensor housing which is sealed in relation to the process vessel by a membrane permeable to the respective analyte. The membrane in this instance represents the sterile barrier. The receptors may thereby be present immobilized on the subsequently introduced working electrode, or in a solution received into the reaction chamber. The sterile barrier may not be destroyed upon introduction of the receptors, which makes the handling of such inline sensor arrangements difficult.

In addition to the difficult handling, what is also disadvantageous with these inline sensor arrangements known from the literature is that a fluctuating measurement performance of the biosensors is observed. One reason for this is that the quantity of the subsequently introduced receptors is difficult to reproduce. The previously known inline sensor arrangements that comprise biosensors are not practicable— in particular, not with regard to applications for monitoring industrial processes.

In the field of single-use technologies that are ever more frequently used for bioprocesses, adapters or connectors have become known which enable the introduction of sensors that have been sterilized in advance (by means of gamma radiation, for example) into a likewise pre-sterilized, single-use bioreactor (single-use fermentor). However, these connectors are often not accepted or not usable for application in a process vessel of a conventional process plant, said process vessel being used repeatedly for a plurality of process batches, which process vessel is cleaned regularly and sterilized according to one of the SIP sterilization methods described further above.

For example, the PALL Corporation, Port Washington, USA, offers connectors under the designation, "Kleenpak II Sterile Connectors," that serve for the introduction of fluids or probes or sensors into a single-use process vessel. These connectors consist of two elements that can be connected to one another, wherein, in the unconnected state, both elements are respectively sealed, in their connection region, with a removable strip. The removable strips consist of aluminum foil with polyester coating. To introduce a probe into the bioprocess, the first element of the connector may be connected to the process vessel and be sterilized with this; the second element containing the probe may be sterilized with a gamma sterilization or an autoclaving. To introduce the probe, the two connector elements are only loosely connected to one another, after which the removable strips are removed by pulling them off laterally; the two elements are subsequently tightly connected to one another, and, finally, the probe is slid, through the first element of the connector, into the process vessel.

It is a significant disadvantage of these connectors that the connection between the two elements does not take place with a high certainty of being aseptic, since the two outer surfaces of the removable strips of the elements are not sterile or sterilizable, and thus a contamination risk is present upon removing these strips. Furthermore, the contamination risk is increased in that the two elements are not tightly connected to one another directly after the removal of the removable strips, whereby a contamination due to the non-sterile environment cannot be excluded.

These connectors are also not designed for reusable, stainless-steel process vessels that can be sterilized with SIP methods.

SUMMARY

It is thus the aim of the present disclosure to specify an inline sensor arrangement that overcomes the described disadvantages. The disadvantages of commissioning an inline sensor arrangement according to the prior art are, additionally, to be overcome. The inline sensor arrangement should preferably also be universally usable in repeatedly used, cleanable, and sterilizable process vessels, and allow the safely aseptic introduction of a sensor element of the inline sensor arrangement into a process vessel for measurement of the measurand in a medium contained in the process vessel. The inline sensor arrangement should preferably be suitable for introducing a biosensor with biological detection elements which do not withstand superheated steam sterilization into a process vessel to be sterilized at high temperatures.

The inline sensor arrangement according to the present disclosure for the detection of measured values of a measurand representing an analyte content of a measurement medium comprises: a sensor which is designed to generate and output a measurement signal correlated with the measurand, wherein the sensor has at least one sterile sensor element provided for contact with the measurement medium; and a housing surrounding the at least one sensor element, which housing encloses the sensor element in a chamber that is sealed tightly against an environment of the housing, and wherein the chamber contains inside it a gas volume that is designed such that an influence of harmful substances—in particular, of reactive nitrogen and/or oxygen species—on the at least one sensor element is largely prevented.

This sensor arrangement enables the aseptic introduction of heat-labile sensors into a process vessel that has previously been heat-sterilized, while maintaining the functionality of the sensors. This is possible via the use of the inline sensor arrangement, described in the following, which contains a sensor element located inside a tightly-sealed, sterile chamber, said sensor element likewise being sterile; or which enables the sterilization of the inside of the chamber, including the sensor element, by means of beta or gamma radiation, which protects the sensor element located in the sealed chamber from damage due to an external heat sterilization of the inline sensor arrangement, e.g., while the inline sensor arrangement is tightly connected to the process vessel; and which enables the aseptic contact between the sensor element and a medium contained in the process vessel, in that the chamber is opened to the inside of the process vessel in the sterilized region of the housing exterior. Because the housing exterior is heat-sterilized—in particular, a region of the housing exterior that is brought into contact or is in contact with the inside of the process vessel that is to be kept sterile—the sterile sensor element arranged in the chamber may safely come into aseptic contact with the inside of the process vessel, and, if applicable, be introduced into this, via the opening of the housing in this region. Since the analyte-sensitive sensor element, i.e., the sensor element that is designed to detect a measurand correlated with the analyte content, is tightly sealed in the chamber during the heat sterilization of the housing exterior, it is protected, at least during the heat sterilization, against a sterilization medium—for example, superheated steam—that contacts the housing exterior in the course of the heat sterilization.

Since the gas volume within the chamber is designed such that an influence of harmful substances—in particular, of reactive nitrogen and/or oxygen species—on the at least one sensor element is largely prevented, damage to the sensor element, due to reactive compounds attacking the sensor element during sterilization of the inside of the chamber, including the sensor element, with beta or gamma radiation and/or during a sterilization via heat sterilization, is largely eliminated. This is particularly advantageous if the sensor element has biological detection elements that may be irreversibly damaged by such reactive harmful substances. It has been shown that, given the presence of oxygen and nitrogen in the housing chamber during a sterilization of the sensor element arranged in the chamber via beta or gamma radiation, reactive species—for example, reactive oxygen or nitrogen species or nitrogen oxides—may be formed in the gas volume of the chamber that may lead to damage of the sensor element. A temperature increase inside the chamber during the heat sterilization of the housing exterior may intensify this damage.

In an advantageous embodiment, the gas volume inside the chamber is largely made up of an inert gas—preferably, of one or more noble gases.

The gas volume inside the chamber advantageously contains oxygen and/or nitrogen in a volume fraction of respectively less than 1 vol %—preferably, respectively less than 0.5 vol %, and, more preferably, respectively less than 0.1 vol %.

Additional or alternative agents for eliminating oxygen and/or other gaseous harmful substances—in particular, for the elimination or adsorption of nitrogen oxides and/or other reactive nitrogen and/or oxygen species—may be arranged inside the chamber.

In the process of elimination, the harmful substance is removed via a chemical reaction. The agents for eliminating oxygen, for example, are based upon the oxidation of the corresponding agent. These are, then, often also referred to as oxygen absorbers. By contrast, in the process of the adsorption, the harmful gas is bound via a physical process to the surface of the corresponding agent, or the harmful gas adheres to the surface.

Agents for the elimination may, for example, be oxygen absorbers such as iron, ascorbic acid, photosensitive polymers (trade name Zero2 of the CSIRO company, Canberra, Australia), or enzymes. Iron may be present within the chamber in powdered form—possibly together with a halide-containing catalyst—open or in containers—in particular, with a gas-permeable, possibly flexible, wall. Additional non-metallic, organic reducing agents (antioxidants), e.g., ascorbic acid, ascorbate salts, catechol or enzyme systems, such as glucose oxidase or ethanol oxidase, may be considered absorbents. For the elimination of oxygen or other harmful substances, radical scavengers may also be considered.

Additional agents for the elimination of oxygen of other harmful substances are isoprenoids, cartonoids, vitamin E, provitamin A, vitamin C, coenzyme Q10—optionally, synthetically esterified—proteins such as albumins, catalase, superoxide dismutase.

Potassium permanganate may be considered for the elimination of nitrogen oxide. This may be applied to a carrier material—for example, aluminum oxide $Al_2O_3$.

Agents for adsorption may be adsorbents such as activated charcoal or zeolites. Inorganic harmful substances may, for example, be adsorbed by activated charcoal fabric with copper impregnation. This is commercially available under the trade name ACC-Cu, type: IAC 442, from the company Infiltec GmbH, Speyer am Rhein, Germany.

The following, commercially-available products from the Mitsubishi Gas Chemical Company (MGC), Tokyo, Japan, which contain both agents for elimination and for adsorption, are also suitable for the elimination of oxygen or adsorption of oxygen-containing, gaseous reactive substances or other harmful substances such as NOx, SOx, HCl and NH3: RP (Revolutionary Preservation)-Agent type RP-K: mixture of activated charcoal, unsaturated organic components, diatomaceous earth, polyethylene, Ca(OH)2, as well as an absorbent graphite compound for the elimination of oxygen and adsorption; RP-Agent type RP-A: mixture of unsaturated organic components, zeolite, polyethylene, activated charcoal, and CaO.

As was already explained further above, the inline sensor arrangement is, in particular, designed to aseptically introduce a sensor element—in particular, a heat-labile sensor element—into a process vessel that was heat-sterilized beforehand. For this, the inline sensor arrangement may be integrated into a wall of a process vessel—for example, by means of a fitting or a vessel connection. Via the inclusion of the sensor element in a housing chamber that is tightly sealed with respect to the environment, the likewise sterile sensor element may be protected against the influence of the sterilization medium during a heat sterilization of the housing exterior of the housing that is in contact or to be brought into contact with the inside of the process vessel, which may take place together with the heat sterilization of the inside of the process vessel, for example, and thus the functionality of the sensor element may, essentially, be preserved. Via the design according to the present disclosure of the gas volume inside the chamber, protection of the sensor element from damage due to reactive oxygen and/or nitrogen species or other harmful substances—in particular, during the heat sterilization—is precluded. As has been described further above, by opening the housing, the sensor element may subsequently be aseptically brought into contact with the inside of the process vessel, or with a measurement medium located therein, in a region, located within the process vessel, that is heat-sterilized, which region is, in particular, heat-sterilized together with said process vessel.

In order to ensure that the sensor is not externally exposed to high humidity during the heat sterilization of the housing, the housing of the inline sensor arrangement may be designed, and the chamber sealed against the environment, such that, during the external heat sterilization of the housing at a temperature of 110° C., the relative humidity prevailing within the housing does not exceed a value of 77%—preferably, of 23%, more preferably, of 3%, and, even more preferably, of 1%.

The inline sensor arrangement may have at least one humidity sensor, which is designed to detect measurement values representing a relative humidity prevailing within the chamber. The inline sensor arrangement may additionally be designed to detect, by means of the humidity sensor, a curve of the measurement values representing the relative humidity prevailing within the chamber, at least during the implementation of a heat sterilization of the inline sensor arrangement.

The housing may comprise a wall made up of one or more housing components that tightly encloses the chamber and forms a barrier against the diffusion of water vapor into the chamber. A mean water vapor permeability of the wall, i.e., a mean value of the water vapor permeability of the components forming the wall, at a temperature of 110° C., a pressure difference of less than 5 bar prevailing between the chamber and the environment of the housing wall, and a difference in the relative humidities prevailing in the chamber and in the environment of the wall of more than 67%, advantageously amounts to less than 420 g/(m²d)—preferably, less than 125 g/(m²d), more preferably, less than 15 g/(m²d), and, even more preferably, less than 6 g/(m²d).

In order to keep the humidity in the chamber low, the chamber may contain a desiccant—for example, silica gel or zeolite.

It is also possible that the inline sensor arrangement comprises at least one feed line, opening into the chamber, for an anhydrous or low-water fluid—in particular, pure nitrogen or air having a water content of less than 50 ppmv (parts per million by volume) H2O, and, more preferably, less than 5 ppmv H2O. The feed line may comprise a sterile filter arranged in the flow path of the fluid. It may be connected to a reservoir that contains the fluid—in particular, nitrogen or air. A discharge line for the fluid, which, preferably, likewise comprises a sterile filter, may additionally open into the chamber. The feed line and discharge line are preferably arranged outside of the process vessel.

In addition or as an alternative to the measures described in the preceding for ensuring a low relative humidity within the chamber, the at least one sensor element may, at least temporarily, be thermally decoupled, or able to be thermally decoupled, from the environment of the housing exterior of the housing. For example, it may be thermally decoupled from the housing exterior of the housing such that, during the action of a medium, with a temperature of 110° C., on at least one partial region of the housing exterior over a time period of 15 min, the temperature of the sensor element, starting from an initial temperature of the sensor element of 25° C. at the beginning of this time period, increases by less than 55° C.—preferably, by less than 35° C., and, more preferably, by less than 10° C. For example, such conditions occur with a heat sterilization of the housing exterior, e.g., in the context of an SIP method implemented in a process vessel into which the inline sensor arrangement is integrated. In this instance, the medium may be dry hot air or superheated steam, for example.

The inline sensor arrangement may be provided with at least one temperature probe/sensor that is designed to determine the temperature curve of the at least one sensor element—in particular, during a heat sterilization of at least one partial region of the housing exterior.

The thermal decoupling may, for example, be achieved via a thermal isolation or thermal insulation of the sensor element from the exterior of the housing, whereby the quantity of heat transferred between housing exterior and sensor element per time unit is reduced in comparison to an embodiment of the inline sensor arrangement in which no isolation or insulation of the sensor element from the housing exterior is provided, such that the temperature change in the sensor element is accordingly avoided or slowed.

The thermal decoupling is advantageously achieved in that a thermal insulation material is arranged between the sensor element and the housing exterior, and/or in that, at least temporarily, a pressure of less than <100 mbar prevails in the housing. What is understood by a thermal insulation material here is, in particular, a homogeneous material of low thermal conductivity, or an at least two-phase material having gas-filled voids—in particular, a microporous filler material. The material of low thermal conductivity may advantageously have a thermal conductivity of ≤0.5 W m−1 K−1. The housing advantageously forms a gas-tight chamber surrounding the sensor element.

Alternatively or additionally, the inline sensor arrangement may comprise means for active and/or passive cooling of the sensor element, whereby the quantity of heat transferred per time unit between housing exterior and sensor element is at least partially dissipated by the sensor element so that the temperature change in the sensor element is avoided or slowed. For example, these means may comprise a gas cooling, a cooling with coolant fluid, a Peltier cooling, cooling fins, or a different heat sink.

In order to enable a thermal decoupling of the sensor element from the housing exterior via reduction of the pressure within the housing—in particular, to a pressure of less than <100 mbar—the housing may have a gas outlet opening into the chamber for evacuation, which gas outlet can be sealed gas-tight. In this embodiment, with a gas outlet that is sealed gas-tight, the housing forms a gas-tight chamber surrounding the sensor element. The gas outlet may, advantageously, comprise a sterile filter. The gas outlet is, advantageously, arranged outside of the process vessel if the sensor arrangement is integrated into said process vessel.

In a development of this embodiment, the gas outlet may end in a sealable connector—in particular, a reversible sealable connector—which can be connected to a vacuum pump. The housing or the chamber with may therefore be evacuated—for example, immediately before implementation of the sterilization of the process vessel into which the inline sensor arrangement is integrated. Alternatively, it is also possible to integrate an inline sensor arrangement into a wall of the process vessel whose housing has already been evacuated and, with included sensor element, subsequently sterilized with a suitable method. What is understood here by evacuation is, in particular, the reduction of the pressure prevailing in the housing to a value <100 mbar. It is advantageous to implement the sterilization of the housing with included sensor element in the final packaging via gamma radiation. To better ensure that, in the housing, for thermal decoupling of the at least one sensor element from the environment of the housing exterior, a negative pressure prevails, the housing with included sensor element may be vacuum-packed with a vacuum device in the final packaging.

In a further embodiment, the inline sensor arrangement comprises a cooler for at least temporary cooling of at least a part of the inline sensor arrangement, said cooler serving for at least temporary thermal decoupling of the sensor element from the environment of the housing exterior.

The cooler may be purely passive in nature; for example, it may comprise a heat sink in thermally conductive contact with the sensor element.

Additionally or alternatively, for active cooling of the sensor element, the cooler may comprise at least one thermoelectric transducer—for example, a Peltier element. This is, advantageously, arranged so that it cools a sensitive surface of the sensor element, which surface is designated for contact with the measurement medium in order to perform measurements.

In a further embodiment, the cooler may comprise a fluid cooling. This may advantageously have a channel structure, through which fluid can flow, in a sensor element carrier on which the sensor element is arranged, and/or in the housing wall of the housing.

In order to improve the thermal decoupling, it is advantageous if the housing or at least one or more components forming the housing are made of a thermally insulating plastic having a thermal conductivity of ≤0.5 W m−1 K−1— in particular, are made of PEEK.

To bring the sensor element or a sensitive surface of the sensor element into contact with a measurement medium located outside of the housing, the housing may have a wall region which is designed to bring the sensor element into contact with the environment of the housing. For example, the wall region may be designed to be opened, in order to produce a connection between the sensor element, or between the chamber containing the sensor element, and the environment of the housing. This wall region is arranged in a region of the housing that comprises a housing exterior of said housing that is in or can be brought into contact with the inside of the process vessel.

The sensor element and the wall region may be movable with respect to one another in such a manner that the sensor element may be slid out of the housing.

In an embodiment of the inline sensor arrangement in which the sensor element is arranged on the sensor element carrier, the sensor element carrier may be borne so as to be movable relative to the housing such that a relative movement of the sensor element carrier at the housing causes a transport of the sensor element out of the opened housing.

For example, the housing—in particular, the chamber containing the sensor element—may have a wall region that is designed as a break-off point. To produce a contact between the sensor element and the housing environment, the sensor element carrier may have a point or edge that is designed such that it pierces or cuts open the wall region in case of a movement of the sensor element carrier relative to the wall region which leads to a contact of the end segment of the sensor element carrier with the wall region. For example, this wall region may be designed as a frontal wall of the housing, said wall being in contact with the inside of the process vessel and/or facing toward the process vessel and formed by a membrane or film, for example.

Alternatively, the housing may comprise a cap, a cover, or a sluice arrangement which is movable relative to the housing so that the housing is opened by a movement of the cap, cover, or sluice arrangement relative to an additional housing part such that a contact is established between the sensor element and the environment of the housing. If the inline sensor arrangement is integrated into the process vessel, the cap, the cover, or the sluice arrangement is in contact with the inside of the process vessel and may be sterilized in a heat sterilization together with said process vessel, such that an actuation of the sluice arrangement cannot lead to the inside of the process vessel coming into contact with non-sterile parts or with a non-sterile environment.

As already described in the preceding in conjunction with the commissioning process, the sensor element may have biological detection elements. For example, an enzyme that can be lyophilized while maintaining at least 10% of its activity acts as a biological detection element. For example, the sensor element may comprise glucose oxidase. For example, the sensor may be an amperometric, enzyme-based sensor—in particular, one comprising glucose oxidase.

The housing may be made of glass and/or have at least one metal layer and/or a layer of plastic, and/or comprise a plurality of solid particles—in particular, metal particles—that act, in particular, as a diffusion barrier to water vapor. For example, the metal particles in the form of spheres or platelets may be embedded into a plastic that forms a wall or a seal or a joint or an encapsulation of the housing.

The sensor element may comprise one or more electrodes, wherein conductors contacting the electrodes travel through a channel formed within a sensor element carrier on which the sensor element is arranged.

The sensor may additionally comprise a measurement circuit that is connected to the conductors and is designed to detect an electrical signal correlated with the measurand. In the event that the sensor is designed as an amperometric sensor, the measurement circuit serves to apply a voltage between at least two electrodes of the sensor and to detect the current that thereby flows, and to output this or an electrical signal derived from this as a measurement signal.

The inline sensor arrangement may comprise an evaluation circuit which is designed to determine, from the electrical signals output by the measurement circuit, measurement values of the measurand in the unit of the measurand, and to output via an interface to a superordinate unit or via an indicator device—for example, a display.

The present disclosure relates to a method for producing an inline sensor arrangement according to one of the embodiments described in the preceding. The method comprises the following steps: producing an inline sensor arrangement with a sensor, which is designed to generate and output a measurement signal correlated with the measurand, wherein the sensor has at least one sensor element provided for contact with the measurement medium, and with a housing surrounding the sensor element and at least one section of the sensor element, which housing encloses the sensor element in a chamber that is sealed tightly against an environment of the housing; and sterilization via irradiation by beta or gamma radiation of the at least one sensor element of the inline sensor arrangement that is arranged in the chamber.

The production of the inline sensor arrangement may additionally comprise the tight sealing of the chamber, wherein a relative humidity present in the chamber after the sealing is dimensioned so that, during an external heat sterilization of the housing at a temperature of 110° C. over a time period of 15 min, the relative humidity prevailing within the chamber does not exceed a value of 77%—preferably, of 23%, more preferably, of 3%, and, even more preferably, of 1%.

The gas volume present in the chamber upon tightly sealing the chamber is designed such that an influence of harmful substances—in particular, of reactive nitrogen and/or oxygen species—on the at least one sensor element is largely prevented. For this, the chamber may be filled with inert gas; for example, it may be also be evacuated before the sealing, and the inert gas subsequently introduced. The chamber may also be flushed with the inert gas for a predetermined duration, without first being evacuated. The inert gas is, for example, essentially made up of a noble gas or a mixture of multiple noble gases. It is alternatively or additionally possible that the inert gas contains oxygen and/or nitrogen in a volume fraction of less than 1 vol %—preferably, less than 0.5 vol %, and, more preferably, less than 0.1 vol %.

The method may additionally include the introduction of one or more agents for the elimination of oxygen and other gaseous harmful substances—in particular, for the elimination of nitrogen oxides and/or other reactive nitrogen and/or oxygen species in the chamber, and, in particular, before sealing the chamber.

The method may additionally include the thermal decoupling of the at least one sensor element from the environment of a housing exterior of the housing.

The aim is further achieved via a method for commissioning an inline sensor arrangement as described above. The method comprises the following steps: implementing a heat sterilization of at least one part, comprising a housing exterior of the housing, of the inline sensor arrangement; opening the housing after ending the heat sterilization; and bringing the sensor element into contact with the measurement medium.

The part of the inline sensor arrangement that is subject to a heat sterilization is, for example, the entire region of the inline sensor arrangement that is in or is to be brought into contact with the inside of a process vessel that is to be kept sterile—in particular, the entire region of the housing exterior of the housing that is in contact with the inside of the process vessel that is to be kept sterile. Because the housing exterior is heat-sterilized—in particular, a region of the housing exterior that is brought into contact or is in contact with the inside of the process vessel that is to be kept sterile—the sterile sensor element arranged in the chamber may safely come into aseptic contact with the inside of the process vessel, and, if applicable, be introduced into this, via the opening of the housing in this region. Since the analyte-sensitive sensor element, i.e., the sensor element that is designed to detect a measurand correlated with the analyte content, is tightly sealed in the chamber during the heat sterilization of the housing exterior, it is protected, at least during the heat sterilization, against a sterilization medium—for example, superheated steam—that contacts the housing exterior in the course of the heat sterilization. Due to the composition of the gas volume that was further described in the preceding, it is also protected against attacks by harmful substances. It has been shown that, although biological detection elements of the sensors described above that are used in bioprocess metrology may lose a majority of their functionality in case of high humidity and high temperatures, as occur in a superheated steam sterilization, they essentially retain their functionality with low humidity, even at the temperatures of at least 110° C. that prevail in a heat sterilization. Via The sealed inclusion of the sensor element into the chamber may therefore already contribute to maintaining the functionality of the sensor element in spite of high temperatures with the heat sterilization of the housing exterior, such that the sensor element subsequently introduced aseptically into the process vessel is functional.

The sensor element may be arranged on a sensor element carrier, wherein the housing surrounds—in addition to the sensor element—at least one segment of the sensor element carrier, such that at least this segment is arranged within the chamber formed in the housing.

The measurement signal may be an electrical signal or an optical signal that represents a measurement value or a chronological sequence of measurement values of the measurand.

For commissioning, the inline sensor arrangement may be integrated into a wall of a process vessel before the implementation of the heat sterilization, and the heat sterilization of the inline sensor arrangement may be implemented in a single method step together with a heat sterilization of the process vessel, wherein the housing in contact with the inside of the process vessel, said housing now being sterilized, is opened to the process vessel after the end of the heat sterilization. For example, this may take place within the scope of an SIP process. The integration of the inline sensor arrangement into the wall of the process vessel may take place by means of a fitting or a process connection that is connected tightly—in particular, fluid-tight, i.e., gas-tight and/or liquid-tight—to the inline sensor arrangement. The connection is thereby, preferably, such that the process vessel is sealed fluid-tight against the environment of the process vessel. his is preferably produced by means of one or more hygienic sealing elements that are designed such that their surfaces in contact with the inside of the process vessel can be sterilized by means of an SIP process. For example, this sealing element may be a suitable hygienic molded seal, as they are fundamentally known from the prior art for fittings and retractable assemblies for use in hygienic applications.

The implementation of the heat sterilization may also take place in an autoclave. The inline sensor arrangement may thereby already be connected to the process vessel, and both may be placed in the autoclave and sterilized therein.

To aseptically open the housing and bring the sensor element into contact with the measurement medium, the region of the housing that is in contact with the inside of the process vessel may be designed to be hygienic—in particular, free of edges, ribs, and gaps.

In order to ensure that the sensor is not exposed to high humidity during the heat sterilization, the housing of the inline sensor arrangement may be designed, and the chamber sealed against the environment, such that, during the external heat sterilization of the housing at a temperature of at least 110° C., the relative humidity (also referred to as relative humidity) prevailing within the housing does not exceed a value of 77%—preferably, of 23%, more preferably, of 3%, and, even more preferably, of 1%.

During the heat sterilization, the course of the relative humidity within the chamber including the sensor element may be monitored by means of a humidity sensor of the inline sensor arrangement. The humidity sensor may be part of the inline sensor arrangement.

The housing may comprise a wall made up of one or more housing components that enclose the chamber gas-tight and form a barrier against the diffusion of water vapor into the chamber. A mean water vapor permeability of the housing wall, i.e., a mean value of the water vapor permeability of the components forming the wall, at a temperature of 110° C., a pressure difference of less than 5 bar prevailing between the chamber and the environment of the wall, and a difference in the relative humidities prevailing in the chamber and in the environment of the wall of more than 67%, advantageously amounts to less than 420 $g/(m^2d)$—preferably, less than 125 $g/(m^2d)$, more preferably, less than 15 $g/(m^2d)$, and, even more preferably, less than 6 $g/(m^2d)$.

The wall, or the housing components forming the wall, may be made from a material through which water vapor cannot diffuse, or can diffuse to only a limited extent; for example, such a material may be glass, plastic, or metal. The use of a composite material, e.g., a multilayer composite material, is also possible. A multilayer composite material that is suitable for this purpose may, for example, comprise at least one plastic and/or metal layer, or a metallized coating. Multilayer materials made of various plastic materials, such as composite films, are also usable, e.g., PET-PE, PET-PVCD/PE or PE-EVOH-PE, or plastic composite films having metallic layers—for example, a composite of PET-aluminum-PE or aluminum-PET-aluminum. In addition to this, single-layer or multilayer plastic materials coated with aluminum oxide or silicon oxide may be used—for example, PET-SiOx/PE.

The sensor element may have at least one biological detection element for the analyte. Biological detection elements may be proteins such as enzymes or antibodies, DNA/RNA fragments, cell organelles, or whole cells and microorganisms. For example, the biological detection element binds the analyte specifically or enters into a chemical reaction with the analyte. For example, the sensor may be an amperometric enzyme sensor. For example, as a detection element, the sensor element may have an enzyme that can be lyophilized while maintaining at least 10% of its activity. The sensor may be an enzyme-based glucose sensor—for example, with glucose oxidase as a detection element. Considered here is a glucose sensor comprising glucose oxidase that is produced and offered for sale under the designation, B.LV5, B.IV4, by Jobst Technologies GmbH, Freiburg, Germany. These amperometric, enzyme-based sensors may also comprise lactate oxidase as a detection element for lactate sensors, glutamate oxidase for glutamate sensors, and glutaminase for glutamine sensors.

In addition or as an alternative to the protection against too high a humidity, it may be advantageous to thermally decouple the sensor element from the environment of the housing, i.e., the environment of a housing exterior of the housing, at least temporarily—in particular, during the implementation of the heat sterilization. The sensor element may—in particular, during the method described in the preceding for commissioning—be thermally decoupled from the environment of the housing until after the end of the heat sterilization. The sensor element is thereby, advantageously, thermally decoupled thermally from the environment of a housing exterior of the housing, such that, during the heat sterilization of the inline sensor arrangement, the temperature of the sensor element rises to less than 80° C.—preferably, to less than 50° C., and, more preferably, to less than 35° C. In addition or as an alternative to ensuring a low relative humidity within the chamber, this may serve to avoid a negative effect on the measurement properties of the sensor element—in particular, insofar as it comprises biological detection elements.

For the purpose of the at least temporary thermal decoupling of the sensor element from the environment of the housing, the sensor element may be arranged at a distance from the volume of the process vessel that is to be sterilized, and from the parts contacted by the sterilization medium—for example, during a heat sterilization. For example, the process vessel may have a connection that surrounds a connection space communicating with the process vessel, and that is connected before the implementation of the heat sterilization to a process connection of the inline sensor arrangement that is complementary to said connection. The process connection is thereby connected to the housing of the inline sensor arrangement such that the sensor element is arranged on a side external to the connection space, said side facing away from the process vessel, when the process connection and the connection of the process vessel are connected to one another. For example, a face surface of the housing of the inline sensor arrangement may seal the connection space if the connection of the process vessel is connected to the process connection of the inline sensor arrangement. In this instance, only the face surface of the housing comes into contact with the sterilization medium and is heated by this, whereas the sensor element behind the face surface is arranged at a distance from said face surface and thus is exposed to lower temperatures. In this way, a thermal decoupling of the sensor element from the inside of the process vessel, which may be exposed to a heat sterilization, may be achieved.

Upon its commissioning, the inline sensor arrangement may advantageously be cooled before the heat sterilization—preferably, to less than 8° C., more preferably, to less than −13° C., and, more preferably, to less than −20° C. During the heat sterilization, the temperature curve of the at least one sensor element may be monitored via at least one temperature probe/sensor of the inline sensor arrangement.

BRIEF DESCRIPTION OF THE DRAWINGS

The present disclosure is explained in further detail below on the basis of the exemplary embodiments shown in the figures. Shown are.

DETAILED DESCRIPTION

Figure 1:
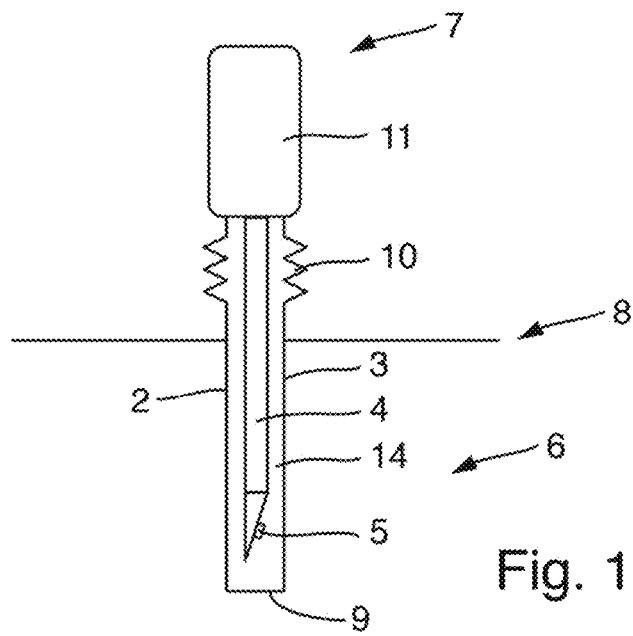
FIG. 1 shows a schematic illustration of a first exemplary embodiment of an inline sensor arrangement integrated into the wall of a process vessel.

Schematically depicted in FIG. 1 is an inline sensor arrangement 7 that is integrated into the wall of a process vessel 8—for example, a conduit or a fermentor. A biotechnological process that is to be protected against contamination is implemented in the process vessel 8. For integration of the inline sensor arrangement 7 into the process vessel 8, the inline sensor arrangement 7 may have a process connection (not shown in FIG. 1) that is connected fluid-tight to a connection of the process vessel 8 that is complementary to the process connection. Alternatively, the inline sensor arrangement 7 may be arranged in a fitting that is attached fluid-tight to a connection of the process vessel 8.

The inline sensor arrangement 7 comprises a sensor that is essentially formed by an analyte-sensitive sensor element 5 and a measurement circuit connected to the sensor element 5. To measure an analytical measurand of a measurement medium, the analyte-sensitive sensor element 5 is designed to be brought into contact with said measurement medium. For example, the sensor element 5 may have one or more electrodes which are modified with biological detection elements. The detection elements may, for example, comprise binding compounds specific to the analyte that are immobilized on the electrode surface. For example, enzymes or proteins are considered specifically binding compounds. The sensor element 5 is arranged on a sensor element carrier 4. In the example shown here, the sensor element carrier 4 is designed in the form of a rod. A void, e.g., a channel extending in the axial direction, may be formed within the rod-shaped sensor element carrier 4, through which void are directed discharge lines (not shown here) that electrically contact the sensor element 5.

At an end facing away from the process, the inline sensor arrangement 7 has an electronic housing 11 in which is arranged the measurement circuit serving for the detection of measurement values. The measurement circuit is connected in an electrically conductive manner to the discharge lines directed through the sensor element carrier 4, and is designed to generate electrical measurement signals correlating to the measurand to be detected. In the example shown here, the sensor of the inline sensor arrangement 7 is designed as an amperometric enzyme sensor. In this instance, the measurement circuit is designed to apply or adjust a voltage between two electrodes of the sensor element 5, and to detect the current thereby flowing through a measurement medium contacting both electrodes. The measurement circuit outputs the detected current, or an—in particular, digital—value derived from this, as a measurement signal. The measurement circuit may be connected to a superordinate evaluation or control unit (not shown) that receives and further processes measurement signals output by the measurement circuit. The electronic housing 10 may have an interface, e.g., an interface comprising a primary side of a plug connector, for connection to the superordinate evaluation or control unit. The evaluation or control unit may be connected to the inline sensor arrangement 7 via a cable that comprises the secondary side of the plug connector.

The inline sensor arrangement 7 comprises an additional housing 2 that surrounds a segment of the sensor element carrier 4 that protrudes into the process vessel and comprises the sensor element 5. In the example shown here, the housing 2 comprises multiple housing components, viz., a tubular shaft 3 that is sealed by a frontal wall 9 at an end protruding into the process vessel 8, and an expansion bellows 10 connected to the shaft 3 at the end of said shaft 3 that is opposite the wall. The frontal wall 9 may be formed by a metal/plastic composite film that is connected via positive substance joining, e.g., by means of an adhesive or a sealing compound, to the tubular shaft 3. On its side opposite the wall 9, the housing 2 is sealed tightly by a sealing compound (not labeled) and connected to the electronic housing 11.

The housing 2 completely encloses the forward segment of the sensor element carrier 4 that comprises the sensor element 5 in a gas-tight chamber 14, such that no connection exists between the volume of the chamber 14 that is enclosed in the housing 2 and the inside of the process vessel 8. The gas-tight chamber 14 contains a gas volume that is designed such that an influence of harmful substances—in particular, of reactive nitrogen and/or oxygen species—on the at least one sensor element is largely prevented. In the present example, the gas volume contains oxygen and/or nitrogen in a volume fraction of less than 1 vol %—preferably, less than 0.5 vol %, and, more preferably, less than 0.1 vol %. The humidity present in the chamber 14 is dimensioned so that the relative humidity contained in the chamber at a temperature of 110° C. is less than 77%. A desiccant, e.g., silica gel, zeolite, or others, may, in addition, be contained in the chamber, in order to further decrease the relative humidity in the chamber 14.

The housing 2 forms a barrier to the diffusion of water or water vapor from the environment into the chamber. The mean water vapor permeability of the housing 2, which, in the present example, is made of multiple housing components made of different materials, at a temperature of 110° C., a pressure difference of less than 5 bar between the environment and the chamber 14, and a difference in the relative humidities within the chamber 14 and the environment, amounts to less than 420 g/m2d, or, preferably, even less. The various materials of the components of the housing 2 are assembled so that the water vapor permeability of the housing 2 is, on average, below this value. For example, PPSU, ECTFE, PEEK, PPS, PFA, or PCTFE may be considered.

Glass, metal, or plastics which have a correspondingly low water permeability may be considered as materials for the tubular shaft 3. For example, these are metals, or plastics that are impermeable to water vapor.

Moreover, composite materials, e.g., multilayer materials that comprise at least one layer of a material that forms a high barrier against the penetrating diffusion of water from the environment, may be considered as materials for a housing wall—in particular, for the tubular shaft or the frontal wall 9. For example, the composite material may comprise a film having a layer of metal, e.g., aluminum, and/or a layer made of a barrier plastic. For example, such a composite material may be a metal-coated plastic. Instead of a continuous layer of the material with high barrier effect, a composite material that is suitable for the shaft 3 or the frontal wall 9 may, moreover, also comprise a plurality of particles made from such a barrier material that are embedded in a base material—for example, a plastic. For example, the embedded particles may be metal particles.

Sealing compounds, adhesives, or seals that seal the chamber 14 may likewise be materials having high barrier effect. In particular, they may be made of a barrier plastic, or they may be formed from composite materials—for example, from a polymer comprising solid particles.

It is possible that a sealing compound or a seal that, compared with the shaft 3 and the frontal wall 9, makes up only a small portion of the wall bounding the chamber 14 are formed from a sealing compound or sealing material that is conventionally used for liquid analysis sensors. If these materials have a low barrier effect for water vapor, this may be compensated for by a material with very low water vapor permeability being chosen for the shaft 3 or the wall 9 such that the water vapor permeability of all components of the housing enclosing the chamber 14 remains, on average, below the cited limit value.

The water vapor permeability of a material is specified in the unit g/m2d. It is gravimetrically determined, based upon DIN 53122-1/DIN 53122-A, for example, in that a testing vessel filled with a desiccant is sealed by a sample made of the material to be examined, and is exposed to a defined testing atmosphere. The quantity of water permeating through the sample is determined via weighing. Related standards are ISO 2528:1995, ASTM E-96.

Before beginning the implementation of a biotechnological process which is implemented under sterile or aseptic conditions, in the process vessel 8, the inline sensor arrangement 7 may be integrated, tightly connected, into the housing wall of the process vessel 8. The chamber 14, as well as the sensor carrier 4 and the sensor element 5, are already sterile at this point in time. A sterilization of the chamber 14 and of the elements arranged therein may take place by means of irradiation with gamma radiation, for example. The sterilization may, advantageously, already be performed by the manufacturer in the manufacturing of the sensor element 5 or of the inline sensor arrangement 7.

The commissioning of the inline sensor arrangement 7 takes place in the following manner:

In a first step, the process vessel 8, together with that region of the exterior of the housing 2 of the integrated inline sensor arrangement 7 that is in contact with the process vessel 8, is heat-sterilized—for example, by means of a superheated steam sterilization. The superheated steam thereby affects only the exterior of the housing 2 which is in contact with the inside of the process vessel. A typical temperature curve of the housing exterior that is exposed to the superheated steam includes a heating phase from an initial temperature, e.g., room temperature (approximately 25° C.), to 140° C. over a time period of 1 h; a phase of 1 h in length, for example, during which the temperature is held at 140° C.; and a subsequent cooldown phase during which the housing is again cooled down to room temperature over a time period of 4 h, for example. In order to achieve a complete sterilization, sealing elements that seal the connection of the inline sensor arrangement 7 to the process vessel 8 are hygienically designed, i.e., their surface regions that are in contact with the inside 6 of the process vessel 8 are entirely accessible and sterilizable by the sterilization medium—superheated steam, in the present example. The housing exterior of the housing 2 that is in contact with the inside of the process vessel 8 is also hygienically designed, i.e., it has no gaps or ribs or edges that are not entirely accessible to the sterilization medium, and therefore are not sterilizable.

After the end of the sterilization, and after the cooldown of the process to temperatures of less than 80° C.—preferably, less than 60° C. or even less than 40° C.—a contact is established between the sensor element 5 or the chamber 14 and the inside 6 of the process vessel 8 in order to enable the detection of measurement values in a measurement medium contained in the process vessel 8 or flowing through the process vessel 8.

In the present example, the frontal wall 9 of the housing 4 that faces toward the process vessel 8 and is in contact with the inside 6 of said process vessel 8 is designed to be so thin that it may be penetrated via a mechanical application of force. The end of the sensor element carrier 4 that faces toward this wall 9, which sensor element carrier 4 has the sensor element 5, has a point or edge. The sensor element carrier 4 is borne so as to be movable in an axial direction—in the example shown here, by means of a wall region, of the housing 2, that is designed as an expansion bellows 10. Here, and in the following description of additional exemplary embodiments, the term, "axial," is used with reference to an axis of cylindrical symmetry of a sensor element carrier or of a tubular housing shaft of the inline sensor arrangement. The expansion bellows 10 may be contracted in such a manner that the difference between the length (measured in the axial direction) of the housing 2 in the relaxed state of the expansion bellows 10 and the length of the housing 2 with a maximally contracted expansion bellows 10 is greater than the distance between the frontal wall 9 and the sensor element 5, wherein this distance corresponds to a path running in an axial direction between the wall 9 and the point of the sensor element 5 that is arranged furthest from the wall 9. The inline sensor arrangement 7 may additionally have arresting elements (not shown in FIG. 1) that fix the expansion bellows in the contracted position. If the expansion bellows 10 contracts, the sensor element 5 thus pierces the wall 9 and projects across the front-side end of the housing 2. In this way, the chamber 14 is opened to the inside 6 of the process vessel 8, and the sensor element is in contact brought into contact with a process medium contained in the process vessel 8 or flowing through this. The establishment of the contact between the sensor element 5 and the inside 6 of the process vessel 8 thereby takes place aseptically, since the sensor element 5 and the inside of the chamber 14 have already been sterilized prior to the opening. Upon opening the wall 9, there is also no possibility of a contact with the non-sterile environment of the process vessel, or with non-sterile parts of the inline sensor arrangement 7. In the contracted position of the expansion bellows 10, the inline sensor arrangement 7 may serve to monitor the measurand to be detected of the measurement medium contained in or flowing through the process vessel 8.

Alternatively, in the commissioning, the inline sensor arrangement 7 together with the process vessel 8 is subjected to a heat sterilization in an autoclave. The sterilized process vessel 8, together with the sterilized inline sensor arrangement 7, may subsequently be installed into a biotechnological plant and be used to perform a biotechnological process. In this embodiment, the aseptic introduction of the sensor element into the process vessel takes place in the same manner as described in the preceding. In particular, here, contact with non-sterile parts or the non-sterile environment is also precluded.

After the conclusion of the biotechnological process, the sensor is discarded, since a re-sterilization of the process vessel 8 with the inline sensor arrangement 7 is not possible according to the exemplary embodiment described here, in which the housing 2 is irreversibly destroyed upon commissioning. If the process vessel 8 is reused in order to perform a new bioprocess, the inline sensor arrangement 7 is first exchanged for an as yet unused, similar inline sensor arrangement 7 with an intact housing 2.

If the components of the housing 2 of the inline sensor arrangement 7, including the chamber 14, have, on average, a water vapor permeability of less than 420 g/(m2d)—preferably, less than 125 g/(m2d), more preferably, less than 15 g/(m2d), or even less than 6 g/(m2d)—so little water vapor penetrates into the chamber 14 during the heat sterilization—for example, with superheated steam—that the relative humidity within the chamber 14 does not exceed a value of 77%, or even markedly less—for example, below 23% or even below 3%—over the entire duration of the heat sterilization. The relative humidity may even remain below 1%, given a suitable material selection of the housing. Such values may also be achieved when the relative humidity of the air enclosed in the chamber 14 in the production of the inline sensor arrangement 7 is up to approximately 30% at room temperature (25° C.). It has been shown that, under these conditions, a destruction of the biological detection elements does not occur, in spite of the high temperatures occurring in the heat sterilization—for example, according to the temperature curve indicated above. For example, this could be demonstrated for sensor elements of enzyme-based glucose sensors that comprise glucose oxidase as biological detection elements—for example, the glucose sensors manufactured and offered for sale under the designation B.LV5, B.IV4 by Jobst Technologies GmbH, Freiburg, Germany.

The housing 2 may advantageously have an outer diameter of approximately 12 mm. Many standard fittings that are used in process metrology for integration of sensors into the walls of process vessels are designed to accept rod-shaped sensors having an outer diameter of 12 mm. If the housing 2 has an outer diameter of 12 mm, it may be integrated into the wall 9 of the process vessel 8, without further measures, by means of such conventional fittings.

The manufacturing of the inline sensor arrangement 7 may take place such that the sensor element carrier 4 with the sensor element 5 arranged thereon is introduced into the tubular shaft 3, which is already firmly connected to the wall 9 and the expansion bellows 10, while the housing 2 is still open on its side situated opposite the wall 9. In an additional step, the housing 2 may then be sealed on this side via a sealing compound so as to form the chamber 14 surrounding the sensor element carrier 4 and the sensor element 5, wherein at least the electrical leads contacting the sensor element 5 are directed through the sealing compound, in order to be connected to a measurement circuit outside of the chamber 14. The circuit board comprising the measurement circuit is arranged in the electronic housing 11 that is affixed to the housing 2.

Before sealing the chamber 14, the humidity in the chamber may be adjusted so that the relative humidity within the chamber 14, at a temperature of 110° C., remains below the aforementioned limit values. For example, for this, a dry gas may be enclosed in the chamber 14, and/or a desiccant may be introduced into the chamber 14. The production may, moreover, include the sterilization by means of gamma radiation of the inside of the chamber 14, including the sensor carrier 4 and the sensor element 5. Alternatively, this may take place shortly before the commissioning of the inline sensor arrangement 7 on the part of the operator of the plant in which the biotechnological process to be monitored by means of the inline sensor arrangement 7 is implemented.

Figure 2:
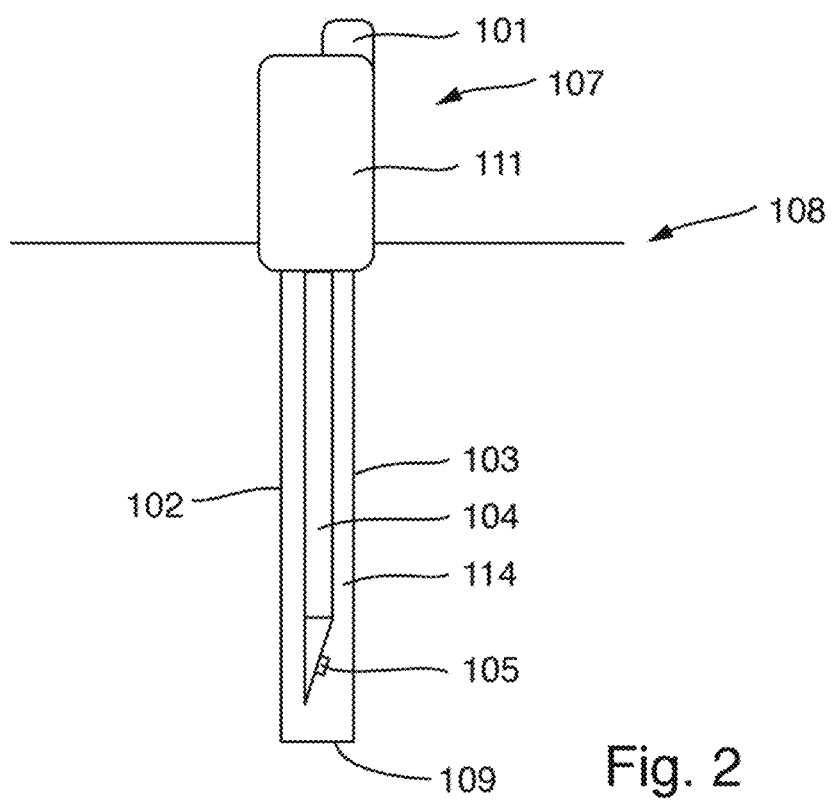
FIG. 2 shows a schematic illustration of a second exemplary embodiment of an inline sensor arrangement integrated into the wall of a process vessel.

FIG. 2 shows a schematic illustration of an additional exemplary embodiment of an inline sensor arrangement 107 that is integrated into the wall of the process vessel 108. For example, the process vessel may be a conduit or a fermentor that is made from a material, e.g., stainless steel, suitable for the process implemented in the process vessel 108—for example, a biotechnological process. The inline sensor arrangement 107 allows a thermal decoupling of a sensor element 105 with biological detection elements from components of the inline sensor arrangement 107 that are exposed to a heat sterilization—for example, a housing exterior. In this way, it may be ensured that, even with sterilization of the inline sensor arrangement 107 by means of heat sterilization, the biological detection elements are exposed to no temperatures that lead to a denaturing of the detection elements, and therefore to a negative effect on the functionality of the sensor element 105.

The inline sensor arrangement 107 comprises a sensor that is essentially formed by an analyte-sensitive sensor element 105 and a measurement circuit connected to the sensor element 105. To measure an analytical measurand of a measurement medium contained in the process vessel 108, the sensor element 105 is designed to be brought into contact with said measurement medium. For example, it may have one or more electrodes which are modified with biological detection elements—for example, substances such as enzymes or proteins that specifically bind to the analyte. The sensor element 105 is arranged on a rod-shaped sensor element carrier 104. A void, e.g., a channel extending in the axial direction, may be formed within the rod-shaped sensor element carrier 104, through which void are directed discharge lines (not shown here) that electrically contact the sensor element 105.

At its end facing away from the process, the inline sensor arrangement 107 has an electronic housing 111 in which is arranged the measurement circuit serving for the detection of measurement values. The measurement circuit is connected in an electrically conductive manner to the discharge lines directed through the sensor element carrier 4, and is designed to generate electrical measurement signals correlating to the measurand to be detected. The measurement circuit may be designed analogously to the measurement circuit of the exemplary embodiment illustrated in FIG. 1. It may likewise be connected to a superordinate evaluation or control unit that receives and further processes measurement signals output by the measurement circuit. The electronic housing 111 may have an interface, e.g., an interface comprising a primary side of a plug connector, for connection to the superordinate evaluation or control unit. The evaluation or control unit may be connected to the inline sensor arrangement 107 via a cable that comprises the secondary side of the plug connector.

The inline sensor arrangement 107 comprises an additional housing 102 which surrounds a section of the sensor element carrier 104, said section comprising the sensor element 105 and protruding into the process vessel 108, and encloses in a chamber 114 that is sealed gas-tight against the environment of the inline sensor arrangement—in particular, relative to the inside of the process vessel 108. In the example shown here, the housing 102 has a tubular shaft 103 and a wall 109 sealing the tubular shaft 103 at the front. On the side situated opposite the wall 109, the tubular shaft is sealed and blocked by a sealing compound. The chamber 114 enclosed in the housing 102 may contain a gas, such as nitrogen, or a gas mixture—for example, air.

Through the electronic housing 111, a gas conduit is directed, the first end of which opens into the inside of the housing 102—more precisely, into the chamber 114—and whose second end has a connector 101. The connector 101 may be attached to the electronic housing 111. The connector 101 may, advantageously, be designed as a sterile connector. In order to reduce the pressure prevailing within the housing 102, the connector 101 may be connected to a vacuum pump. The evacuation of the housing 102, or the decrease in the pressure prevailing in the housing 102 to a value of less than 100 mbar, serves for the thermal decoupling of the sensor element 105 arranged on the sensor element carrier 104 from the exterior of the housing 102, i.e., from the outer surface of the housing wall that faces towards the environment of the housing 102, or from the environment of the exterior of the housing 102. The inside, i.e., the inner housing wall of the housing 102 that faces toward the chamber 114, may be mirrored, as an additional measure for thermal decoupling.

To commission the inline sensor arrangement 107, before beginning the implementation of a bioprocess in the process vessel 108, said inline sensor arrangement 107 may be integrated into its housing wall. The chamber 114, as well as the sensor carrier 104 and the sensor element 105, are, advantageously, already sterile at this point in time. At this point in time, the sensor element 105 is also, advantageously, already thermally decoupled from the environment of the housing exterior, or from the housing wall surface that is directed outwards. A sterilization of the inside of the housing 102 and of the elements arranged therein may take place by means of irradiation with gamma radiation, for example. Just as with the evacuation of the housing 102, the sterilization may, advantageously, already be performed by the manufacturer in the manufacturing of the inline sensor arrangement 107.

For thermal decoupling of the sensor element 104 from the exterior of the housing 102, before or after the integration of the inline sensor arrangement 107 into the process vessel 108, the volume enclosed by the housing 102 may already be evacuated by means of a vacuum pump connected to the connector 101, wherein a pressure of less than 100 mbar is generated in the housing 102. The process vessel 108 may subsequently be sterilized together with the integrated inline sensor arrangement 107—for example, by means of superheated steam sterilization. The superheated steam thereby affects only the exterior of the housing 102. In addition to the insulating properties of the housing wall, the evacuation of the housing 102 produces a thermal insulation of the sensor element 105 from the housing exterior. Given a heat sterilization in which the housing exterior, i.e., the wall surface of the housing 102 that is directed outwards, is exposed to a sterilization medium at a temperature of at least 110° C., temperatures of <80° C.—preferably, <40° C.—occur at the location of the sensor element. These temperatures do not negatively affect the activity of the biological detection elements of the sensor element 102, and therefore the functionality of the sensor, or affect the activity and functionality to such an extent that—in spite of activity reduction of up to 10%—the sensitivity of the sensor is sufficient for monitoring the respective process, or the process medium flowing through.

After the end of the sterilization, and after the cooldown of the housing exterior of the housing 102 or of the environment of the inline sensor arrangement 107 to less than 80° C.—preferably, less than 60° C., or even less than 40°

C.—a contact is established between the sensor element 105 or the chamber 114 and the inside of the process vessel 108 in order to aseptically introduce the sensor element 105 into the process vessel 108, and thus to enable the detection of measurement values in a measurement medium contained in the process vessel 108 or flowing through the process vessel 108. In the present example, the frontal wall 109 of the housing 102 is designed to be so thin that it may be penetrated via a mechanical application of force. The end of the sensor element carrier 104 that faces towards this wall 109, which sensor element carrier 104 has the sensor element 105, has a point or edge. The sensor element carrier 104 is borne so as to be movable in an axial direction, e.g., by means of a ballpoint pen mechanism, wherein the sensor element carrier 104 is movable so far in the axial direction, relative to the wall 109, that the front-side edge or point of the sensor element carrier 104 pierces the wall 109 and is moved so far beyond the front-side end of the housing 102, into the process vessel 108, that the sensor element 105 protrudes into the process vessel 108. In this position, the inline sensor arrangement 107 may serve to monitor the measurand to be detected of a process medium contained in or flowing through the process vessel 108.

In the manufacture of the inline sensor arrangement 107, in which the sensor element 105 on the sensor element carrier 104 is tightly enclosed in the housing 102 or in the chamber 114 formed in the housing 102, the housing 102 or the chamber 114 may already be initially evacuated, and the housing interior with the sensor element 105 may subsequently be sterilized via gamma radiation, for example. Upon commissioning, a user must, then, integrate the inline sensor arrangement 107 only into a wall of a process vessel and may implement the heat sterilization right away.

According to the exemplary embodiment described here, the thermal decoupling of the sensor element 105 from the housing exterior of the inline sensor arrangement 107, said housing exterior being exposed to the sterilization medium—here, superheated steam—serves to prevent a destruction of the biological detection elements during a heat sterilization of the process vessel 108 with the inline sensor arrangement 107 integrated therein. In modifications of the inline sensor arrangement 107 that is described here, in addition to this thermal decoupling, measures may advantageously be taken for keeping the relative humidity within the chamber 114 below a value of 77% or less during the heat sterilization. As was explained further above, a denaturing of the detection elements may thus likewise be prevented. Conceivable measures for avoiding too high a relative humidity in the chamber 114 are, for example: the use of materials having a low water vapor permeability of the components surrounding the chamber 114, as described using the exemplary embodiment illustrated in FIG. 1; the addition of a desiccant into the chamber 114 in the production of the inline sensor arrangement 107; or the feed of an anhydrous or low-water fluid—in particular, of pure nitrogen or air with a water content of less than 50 ppmv H2O, or even less than 5 ppmv H2O—via a sterile filter which the fluid passes before entering into the chamber 114—for example, via the connector 101.

Figure 3:
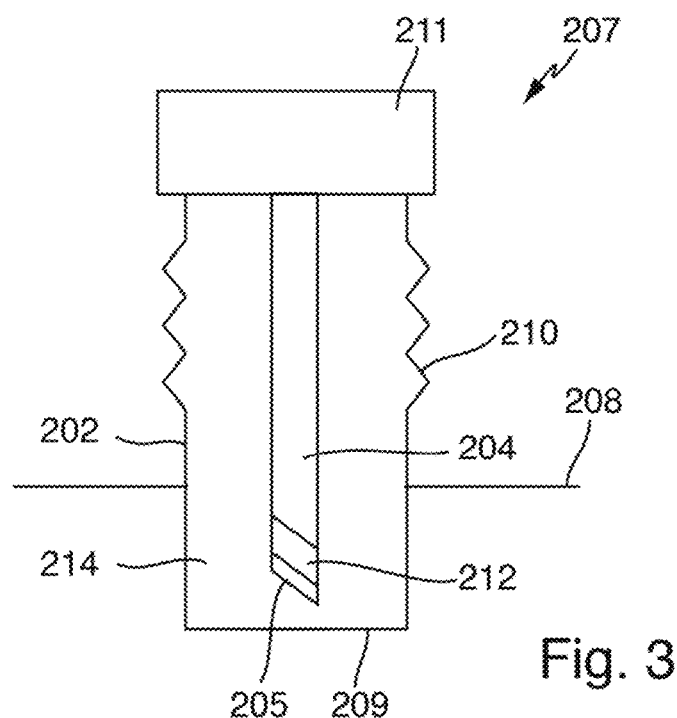
FIG. 3 shows a schematic illustration of a third exemplary embodiment of an inline sensor arrangement integrated into the wall of a process vessel.

Schematically shown in FIG. 3 is a further exemplary embodiment of an inline sensor arrangement 207. This inline sensor arrangement 207 comprises a sensor having a sensor carrier 204 on which is arranged an analyte-sensitive sensor element 205. These may be designed in the same manner as the sensor or the sensor element carrier 4 and the sensor element 5 of the inline sensor arrangement 7 described above using FIG. 1. The sensor element 205 is connected to a measurement circuit via electrical leads that may be directed within a channel formed in the sensor element carrier 204, which measurement circuit is arranged in an electronic housing 211. The measurement circuit is designed to generate a measurement signal dependent upon the measurand detected by the sensor element 205 and to output said measurement signal to a superordinate unit—for example, a measuring transducer. The measurement circuit and the superordinate unit may, for example, be connected to one another via a cable or via a radio connection.

In the exemplary embodiment shown here, the sensor carrier 204 with the sensor element 205 is rigidly connected to the electronic housing 211. The electronic housing 211 seals at the rear side an essentially cylindrical housing 202 that surrounds the sensor element carrier 204 with the sensor element 205 and encloses them gas-tight in a chamber 214. This housing 202 is tightly fastened in a wall of a process vessel 208 by means of a connection device (not shown in detail), so that the inline sensor arrangement 207 is integrated into the process vessel 208. The housing 202 completely partitions the sensor element 205 and the sensor element carrier 204 from the process vessel 208 via enclosure in the chamber 214.

The housing 202 comprises a wall region designed as an expansion bellows 210. The expansion bellows 210 may be contracted in such a manner that the difference between the length (measured in the axial direction) of the housing 202 in the relaxed state of the expansion bellows 210 and the length of the housing 202 with a maximally contracted expansion bellows 210 is greater than the distance between the frontal wall 209 of the housing 202 that faces towards the process vessel 208 and the sensor element 205, wherein this distance corresponds to a path running in the axial direction between the wall 209 and the point of the sensor element 205 that is arranged furthest from the wall 209. The inline sensor arrangement 207 may additionally have arresting elements (not shown in FIG. 2) that fix the expansion bellows 210 in the contracted position.

The wall 209 may be designed as a membrane or as a relatively thin wall segment. For example, the wall may be a moisture-impermeable film that has at least one metallic layer that has low water vapor permeability. The end of the sensor element carrier 204 that faces toward the wall 209 may have an edge or point that is suitable for piercing the wall 209, and thus for opening the chamber 214 towards the process vessel 208, by establishing a connection between the inside of the housing 202 and the inside of the process vessel 208.

A Peltier element 212 that is in planar contact with the back side of the sensor element 205 that faces towards the sensor element carrier 204 serves for thermal decoupling of the sensor element 205 from the housing exterior of the housing 202. Electrical terminals of the Peltier element 212 may be contacted via conductors traveling through the channel formed in the sensor element carrier 204. The Peltier element 212 may thus be operated by means of the measurement circuit. The Peltier element 212 may be in contact with a heat sink, for heat dissipation. This heat sink may comprise a fluid cooling formed within the sensor element carrier 204. For example, the fluid cooling may have a coolant circuit through which fluid flows, formed as a channel structure within the sensor element carrier 204.

In alternative embodiments, it is also possible to actively cool the sensor element 205 solely by means of a fluid cooling. This may be formed within the sensor carrier and/or within the internal space of the housing 202, or within the wall of the housing 202. In another alternative embodiment, the heat sink interacting with the Peltier element 212 may be formed from a material having high heat capacity and/or large surface area—for example, in the form of cooling plates or fins.

Before or after the integration of the inline sensor arrangement 207 into a wall of the process vessel 208, the inside of the housing 202 with the sensor element 205 and the sensor element carrier 204 located therein in the chamber 214 may be sterilized by means of irradiation with gamma radiation.

Upon commissioning of the process vessel 208 and the inline sensor arrangement 207, a superheated steam sterilization may be implemented in the form of an SIP process, with the inline sensor arrangement 207 integrated into the wall of the process vessel 208. At the same time, an active cooling of the sensor element 205 by means of the Peltier element 212 takes place for thermal decoupling of the sensor element 205 from the housing exterior that is exposed to the superheated steam, i.e., the outwardly-directed wall surface of the housing 202. Due to the action of the superheated steam on the outer housing surface of the housing 202, this heats to temperatures up to 120° C. At the same time, the thermally decoupled sensor element 205 heats to at most 80° C.—preferably, less than 40° C.—such that the functionality of the sensor element 205, and therefore of the sensor, is maintained.

After the end of the sterilization—in particular, after the temperature prevailing in the process vessel 208 has lowered to less than 60° C., and, preferably, to less than 40° C.—the cooling of the sensor element 205 may be ended. To bring the sensor element 205 into contact with the inside of the process vessel 208, or with a process medium contained in the process vessel 208, the sensor element carrier 204 with the sensor element 205 arranged thereon may be moved towards the frontal wall 209 of the housing 202 via exertion of a force acting in the axial direction on the electronic housing 211. The expansion bellows 211 is thereby contracted. In this way, the wall 209 may be pierced with the frontal edge or point of the sensor element carrier 204, and thus the sensor element 205 may be brought aseptically into contact with the inside of the process vessel 208. As described in the preceding, the expansion bellows 210 is designed so that the sensor element 205 protrudes beyond the length of the housing 202 upon complete contraction of the expansion bellows 210, such that the sensor element 205 is in contact with the inside of the process vessel 208, and in contact with a process medium located therein, and may detect measurement values of the measurand.

Due to the thermal decoupling of the sensor element 205 during the superheated steam sterilization, a negative effect on the functionality of the sensor element 205 is effectively prevented, even if this comprises biological detection elements in the form of denaturable enzymes or proteins. Additionally or alternatively, the inline sensor arrangement 207 may be designed such that the relative humidity within the chamber 214 remains below a value of 77% during the superheated steam sterilization. For this, the measures already described further above in connection with the exemplary embodiments described in FIG. 1 and FIG. 2 are suitable.

Figure 4:
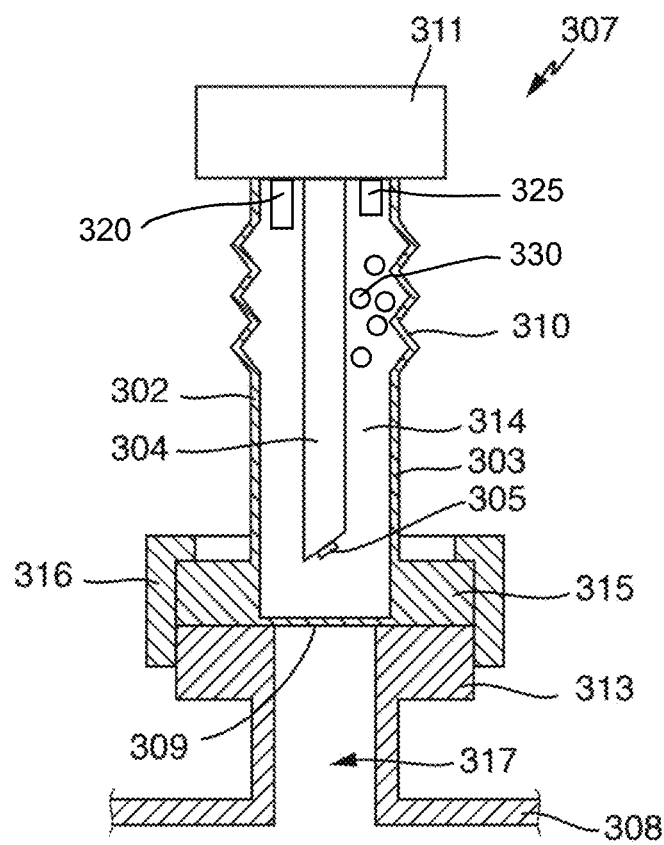
FIG. 4 shows a schematic illustration of a process connection of an inline sensor arrangement that is connected to a connection of a process vessel.

An additional exemplary embodiment of an inline sensor arrangement 307 is illustrated in FIG. 4, in which a thermal decoupling of a sensor element 305 from a housing exterior of the inline sensor arrangement 307 that is in contact with the inside of a process vessel 308 is achieved by the sensor element being arranged at a distance from the process vessel 308.

In this exemplary embodiment, the inline sensor arrangement 307—similar to the inline sensor arrangements of the previously described exemplary embodiments—comprises the aforementioned sensor element 305 that, for example, may comprise an electrode modified with biological detection elements for specific interaction with an analyte. The sensor element 305 is arranged on a rod-shaped sensor element carrier 304. Sensor element 305 and sensor element carrier 304 are surrounded by a housing 302 that comprises a tubular shaft 303 which is sealed at an end facing towards the process vessel 308 via a frontal wall 309. At its other end, the tubular shaft 303 transitions into an expansion bellows 310. The housing 302 is tightly sealed on its side situated opposite the wall 309, e.g., by means of a sealing compound (not indicated here), so that the housing 302 encloses a chamber 314 that is sealed gas-tight, in which chamber 314 are enclosed the sensor element carrier 304 and the sensor element 308.

The inline sensor arrangement 307 moreover has an electronic housing 311 in which is accommodated a measurement circuit which is connected to the sensor element 305, in order to generate and output electrical measurement signals which are correlated with the measurand detected by the sensor element 305. The measurement circuit may be designed like the measurement circuits of the exemplary embodiments described in the preceding using FIGS. 1 through 3.

On its end associated with the process vessel 308, the housing 302 has a process connection 315 that, in the present example, comprises a flange. This process connection 315 is connected to a complementary vessel connection 313 of the process vessel 308—for example, by means of a fixation 316, e.g., a cap nut. In the present example, the process connection 315 and the housing 302 are connected to one another such that the frontal wall 309 of the housing 302 is situated in a plane with the surface of the process connection 315 that abuts against the vessel connection 313. In this way, with a heat sterilization of the process vessel 308 via introduction of a sterilization medium into the process vessel 308, only the frontal wall 309 comes into contact with the superheated steam, but not the tubular side wall 303 of the housing 302 or other components of the inline sensor arrangement 307 that surround the chamber 314.

More generally formulated, this is achieved in that the vessel connection 313, i.e., the tube joined to the vessel and the vessel-side flange connected thereto, surrounds a connection space 317 communicating with the inside 306 of the process vessel 308, which connection space 317 is sealed by the wall 309 at its end facing away from the process vessel 308. In this way, it is ensured that a sterilization medium arriving in the process vessel 308 comes into contact only with the wall 309, but not with the remaining components of the inline sensor arrangement 307 that are in contact with the chamber 314. The process connection 315 is thus connected to the housing 302 of the inline sensor arrangement 307 such that the sensor element 305 is arranged on the side of the housing wall facing away from the process vessel 308, and thus outside of the connection space 317, when the process connection 315 and the vessel connection 313 are connected to one another. In such an arrangement, the sensor element 305 that is arranged to be axially removed from the wall 309 is heated less strongly than with an arrangement as illustrated in FIG. 1, for example, in which—given a heat sterilization of the process vessel 8—the side wall 3 of the housing 2 also comes into immediate contact with a sterilization medium.

The embodiment of the inline sensor arrangement 307 as shown in FIG. 4 further includes a temperature sensors 320, a humidity sensor 325, and also desiccant 330.

The commissioning of the inline sensor arrangement, and bringing the sensor element 305 into aseptic contact with a measurement medium contained in the process vessel 308, may, moreover, take place in the same manner as the commissioning of the inline sensor arrangement 207 described using FIG. 3.

Figure 5:
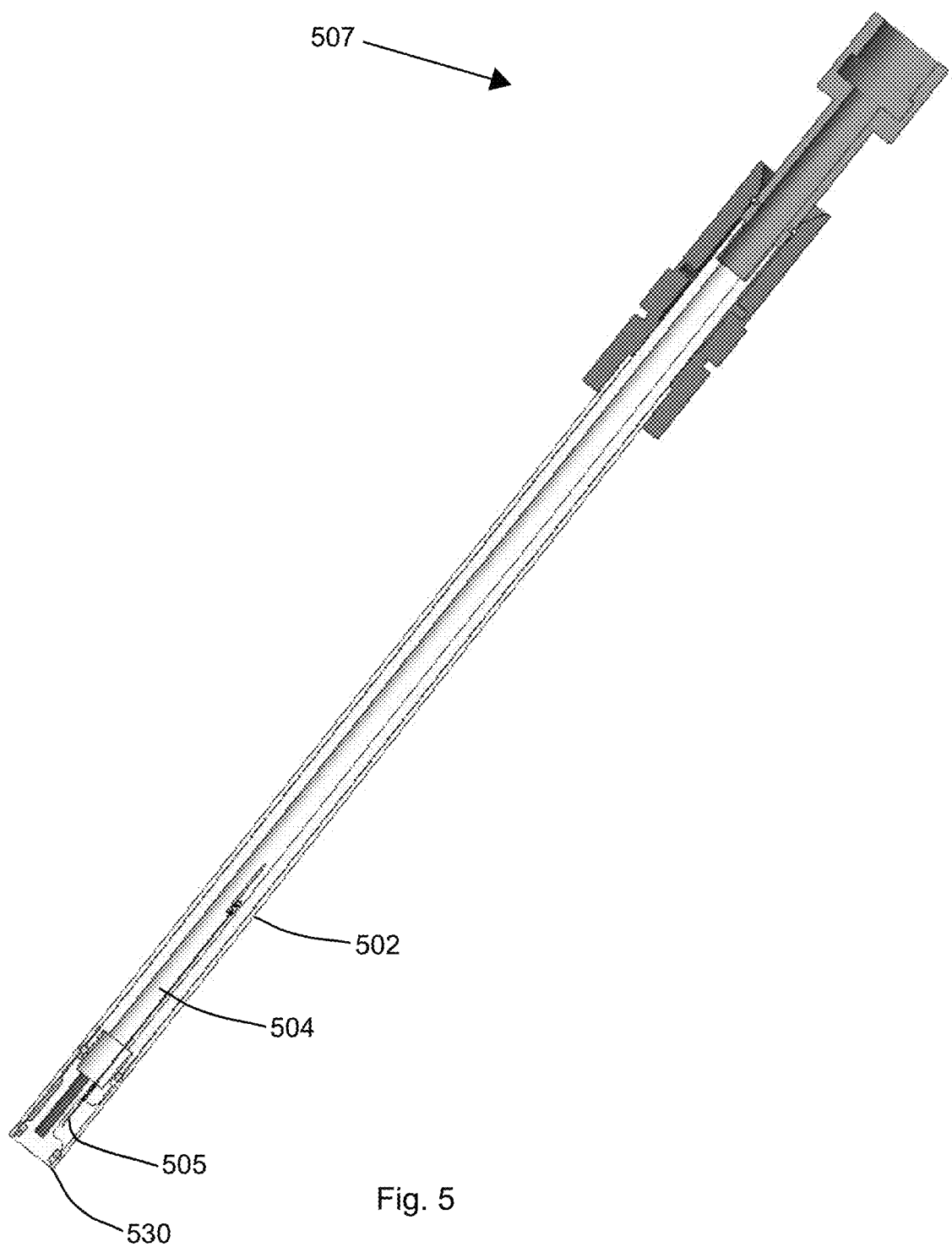
FIG. 5 shows an embodiment of an inline sensor arrangement having a sluice opening in which the sluice is closed.

The inline sensor arrangement 507 as shown in FIG. 5 includes a sluice opening 530 disposed at the end of the housing 502. The sluice opening 530 as shown in FIG. 5 is closed, and the housing 502 is thus sealed against an environment external to the housing 502. Also shown in FIG. 5 is the sensor element 505 disposed on the sensor carrier 504.

Figure 6:
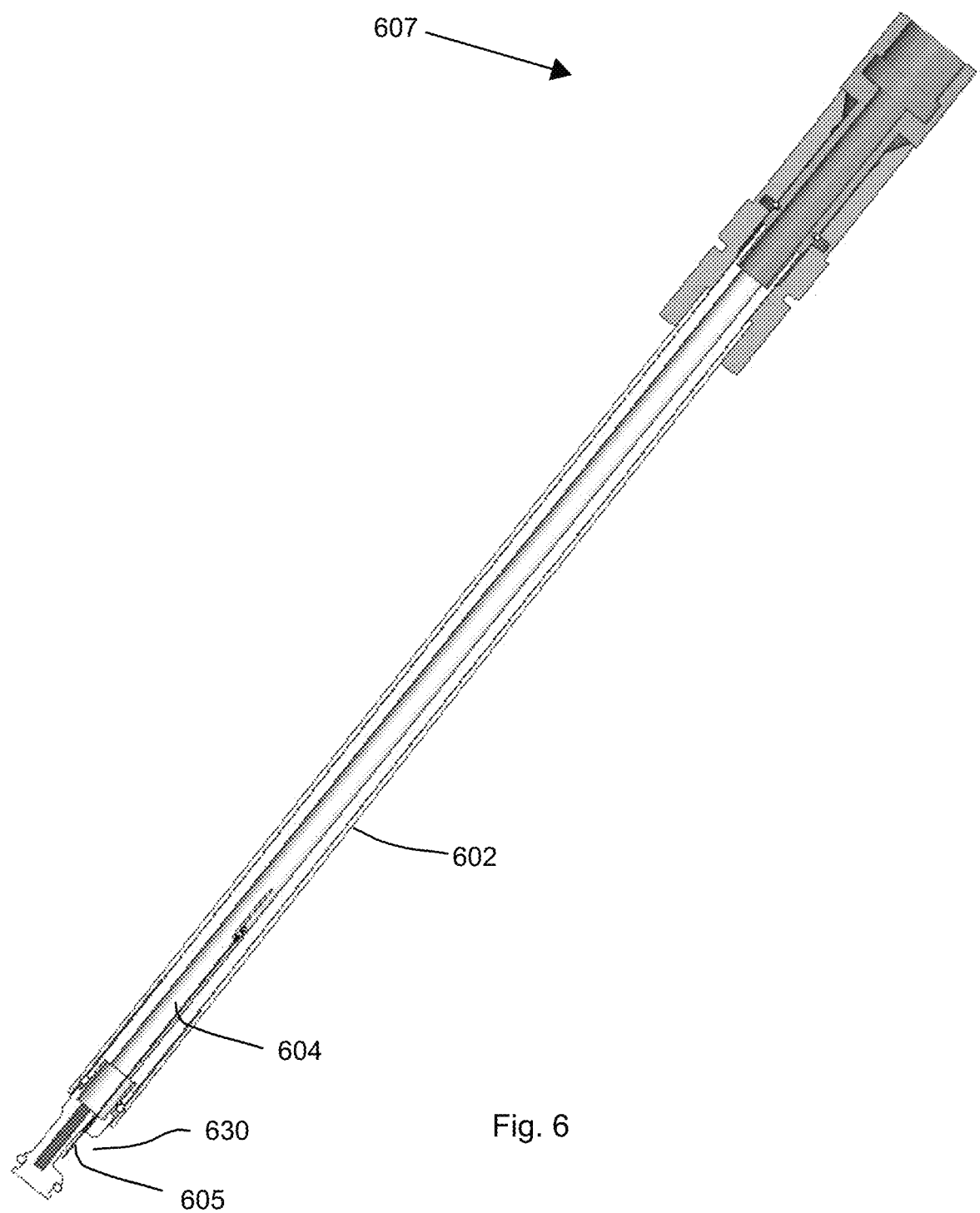
FIG. 6 shows an embodiment of an inline sensor arrangement having a sluice opening in which the sluice is opened.

The inline sensor arrangement 607 as shown in FIG. 6 is identical to the sensor arrangement 507 as shown in FIG. 5. The inline sensor arrangement 607 includes a housing 602 having a sluice opening 630. The inline sensor arrangement 607 further includes a sensor element 605 disposed on a sensor carrier 604. The sluice opening 630 as shown in FIG. 6 is open, in contrast to the sluice opening 530 as shown in FIG. 5 that is closed.

Figure 7:
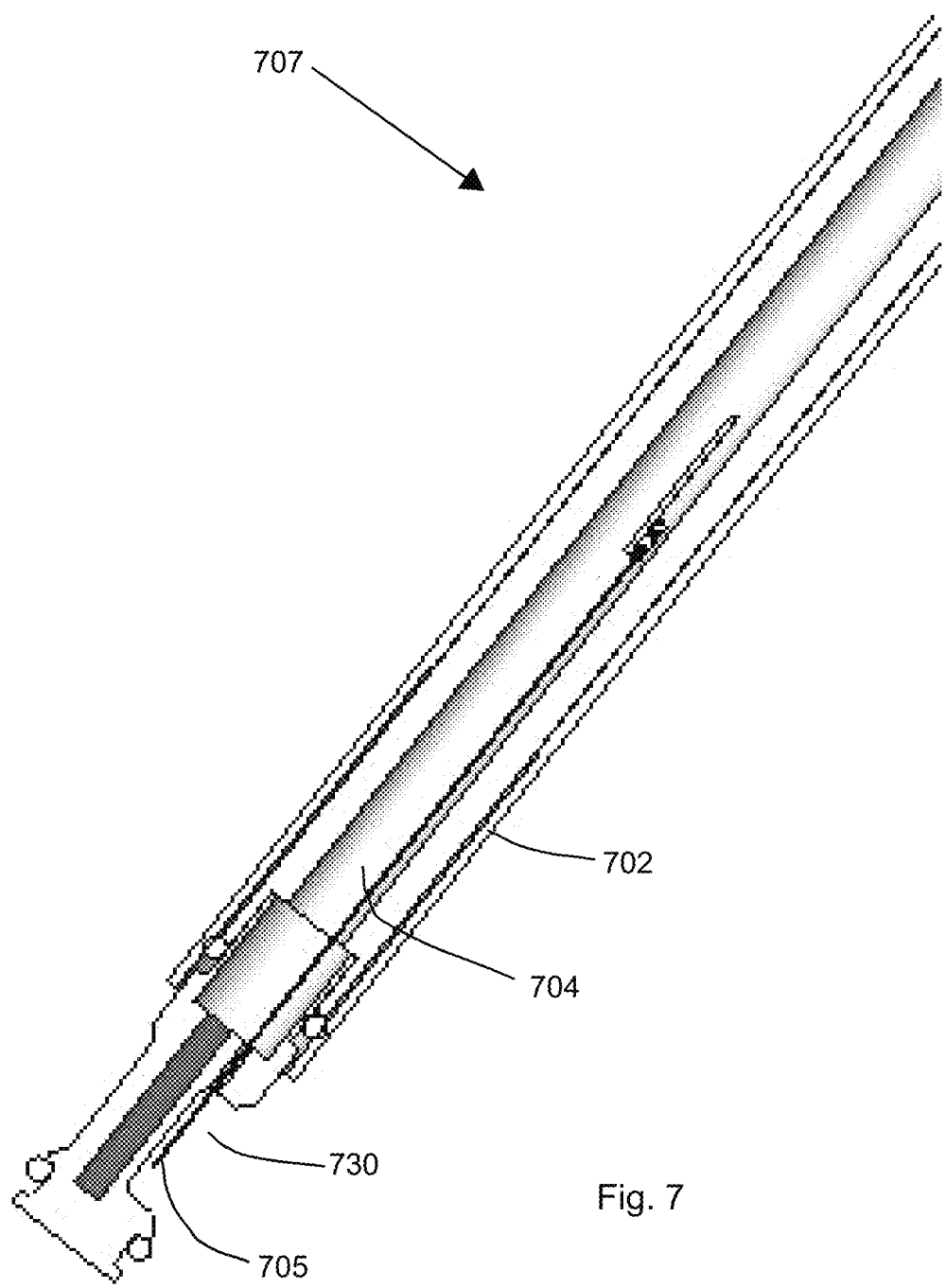
FIG. 7 shows a close-up of an embodiment of an inline sensor arrangement having a sluice opening in which the sluice is opened.

The inline sensor arrangement 707 as shown in FIG. 7 is a close-up of the inline sensor arrangement 607 as shown in FIG. 6. The inline sensor arrangement 707 includes a housing 702, a sensor carrier 704, a sensor element 705, and a sluice opening 730 that is open.

Additional modifications and embodiments of the inline sensor arrangement according to the present disclosure are conceivable. For example, the housing surrounding the sensor element carrier and the sensor element, and separating them from the inside of the process vessel during its sterilization, may also be designed so that the establishment of a connection between the sensor element and the inner space of the process vessel takes place reversibly. For this, for example, the housing wall may comprise an opening which can be reversibly sealed by means of a cover or a cap in order to partition the sensor element from the process vessel, and which may be opened if a connection should be established between the sensor element and the inside of the process vessel. The housing may also be formed by a treatment chamber of an immersion assembly or retractable assembly, or of a sluice device that is designed such that the sensor element with the sensor element carrier may be driven into the process vessel for measurement, or may be driven out of the process vessel into a chamber that is sealed off from the process vessel. The chamber and/or the sensor element carrier may, in this instance, have means for thermal decoupling of the sensor element relative to the exterior, i.e., the outwardly-directed wall surface of the chamber or of the housing, that is in contact with the inside of the process vessel. In all of these embodiments, a repeated use of the housing for bringing a sensor element—in particular, a heat-sensitive and/or moisture-sensitive sensor element—into aseptic contact with a measurement medium which is contained in a previously via heat-sterilized process vessel is possible without disassembly of the entire inline sensor arrangement, i.e., the same housing may remain in the wall of the process vessel for multiple production batches, with sterilization of the process vessel performed between the individual batches. It is thereby possible, in particular, that the housing is permanently integrated into the process vessel, whereas the sensor element carrier and the sensor element arranged thereon can be exchanged for a different, structurally-identical sensor element carrier and a sensor element arranged thereon.

The invention claimed is:

1. An inline sensor arrangement for the detection of measurement values of a measurand representing an analyte content of a measuring medium, the inline sensor arrangement comprising:
    a sterile sensor element embodied to contact the measuring medium and configured to generate and to output a measurement signal correlated with the measurand;
    a sensor carrier having a first end and a second end, wherein the sterile sensor element is disposed on the sensor carrier;
    a housing surrounding the sensor carrier and the sterile sensor element disposed thereon and enclosing the sensor carrier and the sterile sensor element disposed thereon;
    a gas disposed within the housing; and
    the housing further comprises a process connection embodied to connect the inline sensor arrangement with a process vessel having a complementary process connection,
    wherein the housing has a wall region embodied to bring the sterile sensor element into contact with an environment external to the housing.

2. The inline sensor arrangement according to claim 1, wherein the gas within the housing includes one or more noble gases.

3. The inline sensor arrangement according to claim 1, wherein the gas within the housing contains oxygen and/or nitrogen in a volume fraction of respectively less than 1 percent by volume.

4. The inline sensor arrangement according to claim 1, further comprising:
    agents, disposed within the housing, for elimination of oxygen, nitrogen oxides, reactive nitrogen, and oxygen species inside the housing.

5. The inline sensor arrangement according to claim 1, wherein the housing is structured, and the housing is sealed against an environment external to the housing, such that the relative humidity within the housing does not exceed a value of 77% given an external heat sterilization of the housing at a temperature of 110° C. over a time period of 15 min.

6. The inline sensor arrangement according to claim 5, further comprising:
    a humidity sensor disposed within the housing and positioned to detect measurement values representing a relative humidity within the chamber.

7. The inline sensor arrangement according to claim 5, wherein a mean water vapor permeability of the housing amounts to less than 420 g/(m2d) at a temperature of 110° C., a pressure difference of less than 5 bar between the housing and the environment external to the housing, and a difference in the relative humidity in the housing and the environment external to the housing of more than 67%.

8. The inline sensor arrangement according to claim 7, further comprising:
    a desiccant disposed within the housing.

9. The inline sensor arrangement according to claim 1, further comprising:
    a Peltier element disposed on the sensor carrier adjacent to the sterile sensor element and embodied to thermally decouple the sterile sensor element from an environment external to the housing such that, during an action of a measuring medium with a temperature of 110° C. on at least one partial region of the housing exterior over a time period of 15 minutes, the temperature of the sterile sensor element, starting from an initial temperature of the sterile sensor element of 25° C. at the beginning of this time period, increases by less than 55° C.

10. The inline sensor arrangement according to claim 1, further comprising:
a temperature sensor disposed within the housing, wherein the temperature probe is embodied to detect a temperature of the sterile sensor element.

11. The inline sensor arrangement according to claim 1, wherein the second end of the sensor carrier is pointed, and the sensor carrier is embodied to move along an axis;
wherein the wall region is designed to be pierced by the pointed second end of the sensor carrier when the sensor carrier is moved axially and thereby bring the sterile sensor element into contact with an environment external to the housing.

12. The inline sensor arrangement according to claim 11, wherein the sensor carrier with the sterile sensor element and the wall region are movable relative to one another such that the sensor carrier with the sterile sensor element may be slid out of the housing.

13. The inline sensor arrangement according to claim 1, wherein the sterile sensor element includes biological detection elements including at least one enzyme that can be lyophilized while maintaining at least 10% of its functionality.

14. The inline sensor arrangement according to claim 13, wherein the sterile sensor element is an enzyme-based glucose sensor.

15. The inline sensor arrangement according to claim 14, wherein the sterile sensor element is a glucose sensor with glucose oxidase.

16. A method for producing an inline sensor arrangement comprising:
producing an inline sensor arrangement, the inline sensor arrangement comprising:
a sensor element embodied to contact a measuring medium and configured to generate and to output a measurement signal correlated with a measurand representing an analyte content of a measuring medium;
a sensor carrier having a first end and a second end, wherein the sensor element is disposed on the sensor carrier;
a housing surrounding the sensor carrier and the sensor element disposed thereon and enclosing the sensor carrier and the sensor element disposed thereon;
a gas disposed within the housing; and
the housing further comprises a process connection embodied to connect the inline sensor arrangement with a process vessel having a complementary process connection; and
sterilizing via irradiation by beta or gamma radiation the one sensor element that is enclosed in the housing.

17. The method according to claim 16, further comprising:
gas-tightly sealing the housing, wherein a humidity present in the housing after the sealing is dimensioned so that, given an external heat sterilization of the housing at a temperature of 110° C. over a time period of 15 minutes, the relative humidity prevailing within the housing does not exceed a value of 77%.

18. A method for commissioning an inline sensor arrangement, comprising:
providing the inline sensor arrangement including:
a sensor configured to generate and to output a measurement signal correlated with a measurand representing an analyte content of a measuring medium, the sensor having a sensor element embodied to contact the measuring medium;
a housing surrounding the sensor element and enclosing the sensor element in the housing that is sealed against an environment external to the housing; and
the housing further comprises a process connection embodied to connect the inline sensor arrangement with a process vessel having a complementary process connection,
wherein the housing contains a gas volume such that an influence of reactive nitrogen and/or oxygen species on the sensor element is prevented;
performing a heat sterilization of at least one part, including a housing exterior of the housing, of the inline sensor arrangement;
opening the housing after the heat sterilization; and
bringing the sensor element into contact with the measurement medium.

19. The method according to claim 18, further comprising:
integrating the inline sensor arrangement into a wall of the process vessel before the performing of the heat sterilization;
performing the heat sterilization of the inline sensor arrangement in a single method step together with a heat sterilization of the process vessel; and
opening the housing to the process vessel after performing the heat sterilization.

20. The method according to claim 18, wherein the inline sensor arrangement further includes a humidity sensor, and wherein a humidity within the housing is detected using the humidity sensor during the performing of the heat sterilization.

21. The method according to claim 18, wherein the inline sensor arrangement further includes a temperature sensor, and wherein a temperature curve of the sensor element during the heat sterilization is monitored by the temperature sensor.

* * * * *